US008642277B2

(12) United States Patent
Condeelis et al.

(10) Patent No.: US 8,642,277 B2
(45) Date of Patent: Feb. 4, 2014

(54) TUMOR MICROENVIRONMENT OF METASTASIS (TMEM) AND USES THEREOF IN DIAGNOSIS, PROGNOSIS AND TREATMENT OF TUMORS

(75) Inventors: John S. Condeelis, Bronx, NY (US); Thomas E. Rohan, New York, NY (US); Frank B. Gertler, Boston, MA (US); Joan G. Jones, New York, NY (US)

(73) Assignees: Albert Einstein College of Medicine of Yeshiva University, Bronx, NY (US); Massachusetts Institute of Technology, Cambridge, MA (US); Cornell University, Ithaca, NY (US)

( * ) Notice: Subject to any disclaimer, the term of this patent is extended or adjusted under 35 U.S.C. 154(b) by 473 days.

(21) Appl. No.: 12/804,779

(22) Filed: Jul. 29, 2010

(65) Prior Publication Data

US 2011/0059470 A1 Mar. 10, 2011

Related U.S. Application Data

(60) Provisional application No. 61/276,263, filed on Sep. 10, 2009.

(51) Int. Cl.
*G01N 33/567* (2006.01)
*G01N 33/574* (2006.01)
*C07K 16/28* (2006.01)
*C07K 16/30* (2006.01)

(52) U.S. Cl.
USPC ..... 435/7.21; 435/7.23; 435/7.24; 435/40.52; 530/387.7; 530/388.22; 530/388.7; 530/388.8; 530/388.85

(58) Field of Classification Search
None
See application file for complete search history.

(56) References Cited

U.S. PATENT DOCUMENTS

| 6,716,597 B2 | 4/2004 | Gertler et al. |
| 2008/0138805 A1 | 6/2008 | Condeelis |
| 2010/0047240 A1 | 2/2010 | Condeelis et al. |

FOREIGN PATENT DOCUMENTS

| WO | WO2008/097466 | * 8/2008 |

OTHER PUBLICATIONS

Pollard (Nature Reviews Cancer, 2004, vol. 4, pp. 71-78).*
Abstract of Van der Loos et al (Journal of Immunological Methods, 1989, vol. 117, pp. 45-52).*
Torisu et al (2000, vol. 85, pp. 182-188).*
Nishimura et al (Diabetes, 2007, vol. 56, pp. 1517-1526).*
Grum-Schwensen et al (Cancer Research, 2005, vol. 65, pp. 3772-3780).*
Piccart-Gebhart et al (Annals of Oncology, vol. 18, suppl. 12, pp. xii2-xii7), 2007.*
Di Modugno F et al., entitled "Molecular Cloning of hMena (ENAH) and Its Splice Variant hMena+11a Epidermal Growth Factor Increases Their Expression and Stimulates hMena+11a Phosphorylation in Breast Cancer Cell Lines," Cancer Res, Mar. 15, 2007; 67:(6), 2657-2665.
Philippar U et al., entitled "A Mena Invasion Isoform Potentiates EGF-Induced Carcinoma Cell Invasion and Metastasis," Dev Cell. Dec. 2008; 15(6): 813-823.
Robinson B D et al., entitled "Tumor microenvironment of metastasis (TMEM): a novel tissue-based assay for metastatic risk in breast cancer," Future Oncol., 2009, 5 (7), 919-921.
Robinson B D et al., entitled "Tumor Microenvironment of Metastasis in Human Breast Carcinoma: A Potential Prognostic Marker Linked to Hematogenous Dissemination," Clin Cancer Res 2009;15(7), Apr. 1, 2009, 2433-2441.
Goswami S et al., entitled "Identification of invasion specific splice variants of the cytoskeletal protein Mena present in mammary tumor cells during invasion in vivo," Clin Exp Metastasis (2009) 26:153-159.
Wyckoff J B et al., entitled "A Critical Step in Metastasis: In Vivo Analysis of Intravasation at the Primary Tumor," Cancer Research 60, 2504-2511, May 1, 2000.
Goswami S et al., entitled "Macrophages Promote the Invasion of Breast Carcinoma Cells via a Colony Stimulating Factor-1/Epidermal Growth Factor Paracrine Loop," Cancer Res 2005; 65: (12), Jun. 15, 2005, 5278-5283.
Wang W et al., entitled "The activity status of cofilin is directly related to invasion, intravasation, and metastasis of mammary tumors," The Journal of Cell Biology, vol. 173, No. 3, May 8, 2006, 395-404.
Wang W et al., entitled "Identification and Testing of a Gene Expression Signature of Invasive Carcinoma Cells within Primary Mammary Tumors," Cancer Research 64, 8585-8594, Dec. 1, 2004.
Wang W et al., entitled "Tumor cells caught in the act of invading: their strategy for enhanced cell motility," Trends in Cell Biology, vol. 15, No. 3, Mar. 2005, 138-145.

* cited by examiner

*Primary Examiner* — Karen Canella
(74) *Attorney, Agent, or Firm* — Amster, Rothstein & Ebenstein LLP (57) ABSTRACT

Disclosed are methods for determining the risk of tumor cells undergoing metastasis, for assessing the prognosis of a subject undergoing treatment for a localized tumor, and for determining a course of treatment for a localized tumor comprising detecting the presence of an endothelial cell, a macrophage, and an invasive tumor cell in direct apposition in a tumor sample from a subject.

27 Claims, 5 Drawing Sheets

TUMOR MICROENVIRONMENT OF METASTASIS (TMEM) AND USES THEREOF IN DIAGNOSIS, PROGNOSIS AND TREATMENT OF TUMORS

CROSS-REFERENCE TO RELATED APPLICATION

This application claims priority to U.S. Provisional Patent Application No. 61/276,263, filed Sep. 10, 2009, the content of which is incorporated herein by reference in its entirety into the subject application.

STATEMENT OF GOVERNMENT SUPPORT

This invention was made with government support under grant numbers CA100324, CA113395 and GM58801, and Integrative Cancer Biology Program grant number 1-U54-CA112967 awarded by the National Institutes of Health, U.S. Department of Health and Human Services. The government has certain rights in this invention.

BACKGROUND OF THE INVENTION

Various publications are referred to in parentheses throughout this application. Full citations for these references may be found at the end of the specification immediately preceding the claims. The disclosures of these publications are hereby incorporated by reference in their entireties into the subject application to more fully describe the art to which the subject application pertains.

Breast cancer is the most prevalent malignant disease of women in the developed world, apart from non-melanoma skin cancers, with approximately one in eight women in the United States being diagnosed with breast cancer at some time in their lives. Breast cancer mortality is largely attributable to the development of systemic, hematogenous metastatic disease. Although approximately 10-15% of patients have an aggressive form of the disease that metastasizes within three years after initial diagnosis, the clinical manifestations of occult metastatic disease can appear ten or more years later. The consequence is that most breast cancer patients carry a risk for development of metastatic disease throughout the remainder of their natural lives (Ries et al., 2004; Weigelt et al., 2005).

To decrease the risk for the emergence of metastatic tumors, approximately 80% of breast cancer patients are treated with adjuvant chemotherapy. The clinical benefit is a 3 to 10% increase in 15-year survival, depending upon the age of the patient at diagnosis. However, since only about 40% of these patients eventually relapse and develop metastatic disease, there is a significant subset of patients who are unnecessarily subjected to the acute and long-term side effects of current chemotherapeutic regimens (Weigelt et al., 2005). Currently established clinical prognostic criteria such as the histopathological grade of the tumor or tumor size do not successfully predict systemic metastatic potential. Even angiolymphatic invasion and the presence of regional lymph node metastases do not always correlate with subsequent distant spread. This may be because the mechanisms of hematogenous spread are different from those for lymphatic spread. The ability to identify at the time of diagnosis those tumors that have increased likelihood for systemic hematogenous spread would aid in tailoring therapeutic interventions specific for a particular patient and identify those patients who would benefit the most from systemic therapy.

The tumor microenvironment is critical for facilitating metastasis. Utilizing intravital multiphoton imaging in rat and mouse mammary tumors, invasive carcinoma cells have been shown to polarize, move toward, and invade blood vessels (Wyckoff et al., 2007). This polarization and increased motility, leading to invasion of blood vessels by carcinoma cells, requires a paracrine loop involving macrophage-derived epidermal growth factor (EGF) and carcinoma cell-derived colony stimulating factor-1 (CSF-1) (Wyckoff et al., 2004, 2007). Invasive carcinoma cells involved in this paracrine loop yield a distinct gene expression profile, called the invasion signature, and increased cell motility and invasion are the result of alterations in the expression of cytoskeletal regulatory proteins (Wang et al., 2004, 2007).

A key actin polymerization regulatory protein that is part of the invasion signature and that is up-regulated in invasive tumor cells is Mena (Goswami, et al., 2009; Wang et al., 2004, 2007), an Ena/VASP protein family member that is highly conserved across species (Gertler et al., 1996; Krause et al., 2003). Mena regulates cell movement by its ability to protect actin filaments from capping proteins during polymerization (Barzik et al., 2005). Mena is up-regulated in malignant human breast tumors (Di Modugno et al., 2004, 2006, 2007) and is over expressed in a subpopulation of invasive tumor cells of rat and mouse mammary tumors (Wang et al., 2004, 2007), suggesting that Mena plays a central role in regulating breast carcinoma cell invasion. The forced expression of Mena in tumor cells at levels observed in invasive tumor cells has shown that Mena promotes carcinoma cell motility and invasiveness both in vivo and in vitro, and increases intravasation and lung metastasis in vivo. Mena stabilizes invadopodia, actin-rich protrusions that contain proteases, thereby increasing the matrix degradation activity of tumor cells. Importantly, Mena activity potentiates EGF-induced carcinoma cell invasion and membrane protrusion. In aggregate these results indicate that the upregulation of Mena expression in invasive tumor cells enable them to invade and metastasize in response to otherwise benign EGF stimulus levels thereby being more responsive to macrophage signaling (Ulrike et al., 2008).

The density of tumor-associated macrophages (TAM) has been suggested to be a prognostic marker of poor outcome for a variety of carcinomas, including breast carcinoma (Bingle et al., 2002; Condeelis et al., 2006). Macrophages comprise a key component of the tumor microenvironment as facilitators of tumor cell migration and intravasation, stromal matrix breakdown, and angiogenesis (Condeelis et al., 2006). In murine mammary tumors resulting from the expression of the PyMT oncogene in wild-type mice with intact macrophage numbers and function, carcinoma cells, when associated with macrophages, demonstrate an invasive phenotype with increased motility (Wyckoff et al., 2004). Tumor cell motility occurs more than 80% of the time in association with macrophages. Extensive multiphoton time lapse imaging of live tumors has shown that tumor cell intravasation was only observed in association with perivascular macrophages and was not seen in regions of blood vessels without perivascular macrophages. A seven fold reduction in the number of perivascular macrophages in csf1op/csf1op mice was correlated with a 10 fold reduction of circulating tumor cells in the blood of the same mice. Therefore, while tumor cell intravasation in the absence of perivascular macrophages cannot be ruled out, it has not been detected in vivo by direct imaging and may be only a minor kinetic component of intravasation, while perivascular assisted tumor cell intravasation appears to be a major portal of entry of tumor cell into the blood (Wyckoff et al., 2007).

Thus, there is a need for reliable methodologies to predict the risk for metastatic disease in cancer patients in order both to administer proper treatment to patients whose tumors have a high risk of metastasizing and to avoid unnecessary administration of chemotherapy to patients whose tumor had a negligible risk of metastasizing. The present invention addresses this need.

SUMMARY OF THE INVENTION

The invention provides a method for determining the risk of tumor cells undergoing metastasis comprising determining whether or not an endothelial cell, a macrophage, and an invasive tumor cell are in direct apposition in a tumor sample, wherein the risk of tumor cells undergoing metastasis increases with an increase in density of occurrences of an endothelial cell, a macrophage, and an invasive tumor cell in direct apposition in the tumor sample.

The invention further provides a method for determining a course of treatment for a tumor in a subject, the method comprising determining whether or not an endothelial cell, a macrophage, and an invasive tumor cell are in direct apposition in a tumor sample from the subject, wherein an increase in density of occurrences of an endothelial cell, a macrophage, and an invasive tumor cell in direct apposition in the tumor sample indicates that the subject should be treated for a metastatic tumor or wherein a lack of occurrence of an endothelial cell, a macrophage, and an invasive tumor cell in direct apposition in the tumor sample indicates that the subject does not need to be treated for a metastatic tumor.

DETAILED DESCRIPTION OF THE INVENTION

The invention provides a method for determining the risk of tumor cells undergoing metastasis comprising determining whether or not an endothelial cell, a macrophage, and an invasive tumor cell are in direct apposition in a tumor sample, wherein the risk of tumor cells undergoing metastasis increases with an increase in density of occurrences of an endothelial cell, a macrophage, and an invasive tumor cell in direct apposition in the tumor sample.

The invention also provides a method for assessing the prognosis of a subject undergoing treatment for a tumor, the method comprising determining whether or not an endothelial cell, a macrophage, and an invasive tumor cell are in direct apposition in a tumor sample from the subject, wherein an increase in density of occurrences of an endothelial cell, a macrophage, and an invasive tumor cell in direct apposition in the tumor sample indicates a worsening of the subject's prognosis.

The invention further provides a method for determining a course of treatment for a tumor in a subject, the method comprising determining whether or not an endothelial cell, a macrophage, and an invasive tumor cell are in direct apposition in a tumor sample from the subject, wherein an increase in density of occurrences of an endothelial cell, a macrophage, and an invasive tumor cell in direct apposition in the tumor sample indicates that the subject should be treated for a metastatic tumor or wherein a lack of occurrence of an endothelial cell, a macrophage, and an invasive tumor cell in direct apposition in the tumor sample indicates that the subject does not need to be treated for a metastatic tumor.

The invention relates in particular to hematogenic metastasis.

Endothelial cells can be detected, for example, using an agent that is specific for CD31. Macrophages can be detected, for example, using an agent specific for CD68. Invasive tumor cells can be detected, for example, using an agent specific for Mena. The agent can be, for example, an antibody, an antibody fragment, a peptide or an aptamer. Antibody fragments include, but are not limited to, F(ab')$_2$ and Fab' fragments and single chain antibodies. Preferably, the presence of the endothelial cell, the macrophage, and the invasive tumor cell is detected using triple immunohistochemistry.

Preferably, the +++ variant and/or ++ variant of Mena is detected. Preferably, the level of expression of Mena+++ and/or Mena++ is compared to the level of expression of Mena 11a. The invasive tumor cell can be identified, for example, as overexpressing the +++ variant of Mena. The expression of the +++ Mena variant and/or ++ Mena variant can be normalized relative to the expression of protein variants that are not changed in expression in a metastatic tumor. Examples of proteins that could be used as controls include those of the Ena/VASP family that are unchanged in their expression in metastatic cells, including the 140K and 80K isoforms of Mena, and VASP. Other examples of proteins or genes that could be used as controls include those listed as relatively unchanged in expression in Condeelis et al. (2005). Such controls include N-WASP, Rac1, Pak1, and PKCalpha and beta. Preferred controls include the 80K and 140K isoforms of Mena and VASP. The detection of Mena in metastatic tumors has been described, for example, in PCT International Publication No. WO 2008/097466.

Human Mena sequences are indicated below:

```
Mena ++     FYLG                     (SEQ ID NO: 1)

Mena +++    AQSKVTATQD STNLRCIFC     (SEQ ID NO: 2)

Mena 11a    RDSPRKNQIV FDNRSYDSLH R. (SEQ ID NO: 3)
```

The agent can be labeled with a detectable marker. Labeling may be accomplished using one of a variety of labeling techniques, including peroxidase, chemiluminescent, and/or radioactive labels known in the art. The detectable marker may be, for example, a nonradioactive or fluorescent marker, such as biotin, fluorescein (FITC), acridine, cholesterol, or carboxy-X-rhodamine, which can be detected using fluorescence and other imaging techniques readily known in the art. Alternatively, the detectable marker may be a radioactive marker, including, for example, a radioisotope. The radioisotope may be any isotope that emits detectable radiation, such as, for example, $^{35}$S, $^{32}$P, or $^3$H. Radioactivity emitted by the radioisotope can be detected by techniques well known in the art. For example, gamma emission from the radioisotope may be detected using gamma imaging techniques, particularly scintigraphic imaging.

The risk of tumor cells undergoing metastasis rises with the number of times an endothelial cell, a macrophage, and an invasive tumor cell are found in direct apposition in a representative tumor sample. The density of occurrences can be expressed as the number per unit area or per unit volume of the sample. The risk of metastasis can approximately double for each additional ten times an endothelial cell, a macrophage, and an invasive tumor cell are found in direct apposition per unit of sample.

The tumor can be, for example, a secretory epithelial tumor. The tumor can be, for example, a prostate, pancreas, colon, brain, liver, lung, head or neck tumor, or in particular a breast tumor.

The invention also provides kits for determining the risk of tumor cells undergoing metastasis, where the kit includes an agent that specifically binds to CD31 for detecting endothelial cells, an agent that specifically binds to CD68 for detecting macrophages, and an agent that specifically binds to Mena for detecting an invasive tumor cell. Preferably, one or more agent specifically binds to Mena+++, Mena++ or Mena 11a. Preferably, the agents are monoclonal antibodies. Preferably, the kits provide for triple immunohistochemical detection of endothelial cells, macrophages, and invasive tumor cells. The kit can also include positive and negative control samples and instructions for scoring the direct apposition of an endothelial cell, a macrophage, and an invasive tumor cell.

The present invention is illustrated in the following Experimental Details section, which is set forth to aid in the understanding of the invention, and should not be construed to limit in any way the scope of the invention as defined in the claims that follow thereafter.

Experimental Details

Introduction

Figure 1:
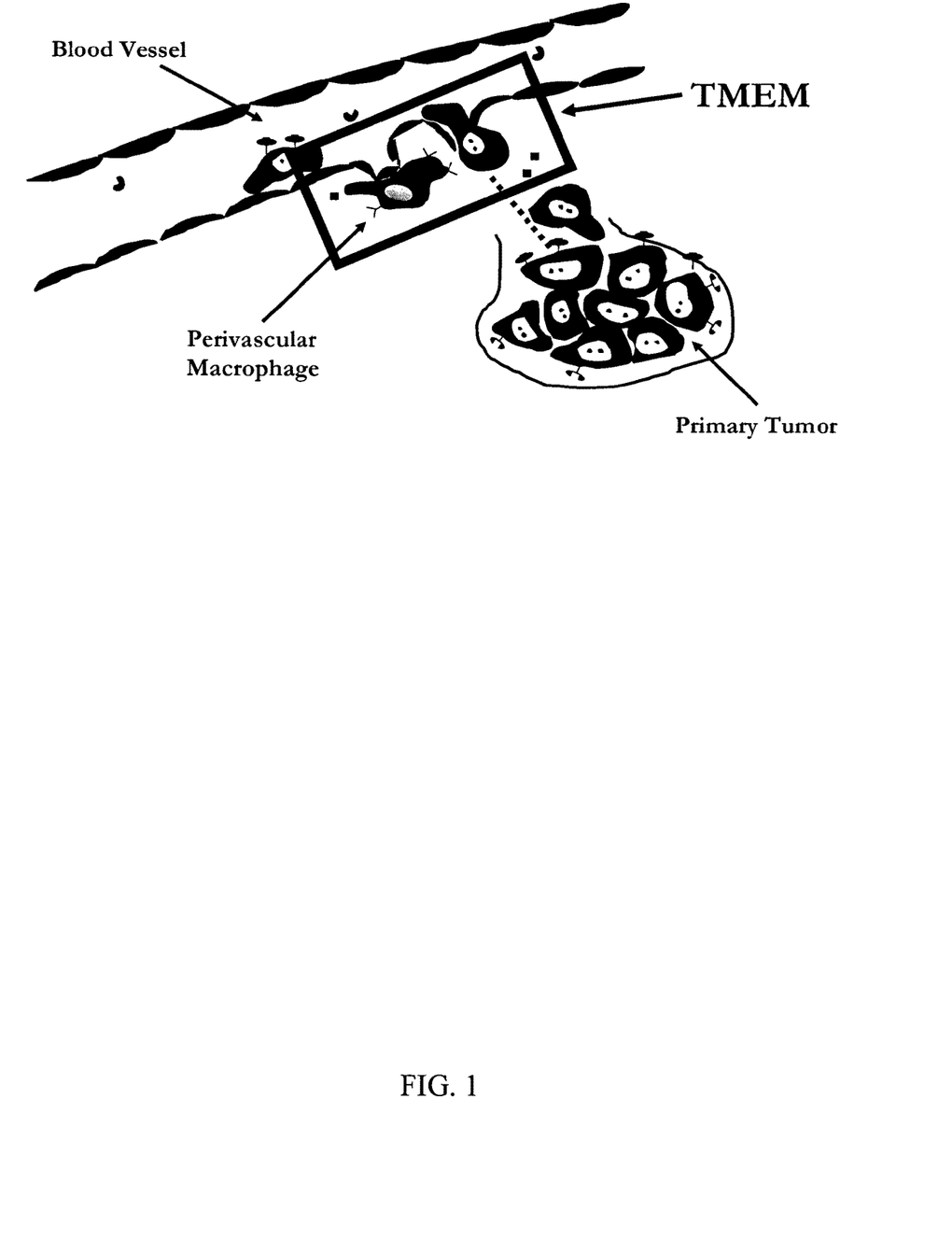
FIG. 1. Definition of the Tumor Microenvironment of Metastasis (TMEM). Cartoon depicting findings in mouse and rat mammary tumors where tumor cells are observed to migrate to blood vessels and intravasate only when in association with perivascular macrophages. The box highlights the anatomic compartment where intravasation occurs, as observed in the rodent mammary tumors, and also corresponds to the areas identified and scored as TMEM in histologic sections in the present study. TMEM is defined as the tripartite arrangement of an invasive tumor cell, a macrophage, and an endothelial cell all in direct apposition. The dashed line illustrates the path taken by migratory tumor cells toward perivascular macrophages, as seen in vivo.

Based on the results with mouse mammary tumors, it is postulated that tumor-associated macrophages (TAM) guide carcinoma cells to blood vessels via the EGF/CSF-1 paracrine loop and that Mena over-expressing carcinoma cells in particular interact with perivascular macrophages to constitute a microanatomic landmark or portal leading to carcinoma cell intravasation. This microanatomic landmark, composed of a perivascular macrophage in contact with a Mena overexpressing tumor cell, is the tumor microenvironment of metastasis (TMEM) (FIG. 1). As disclosed herein, TMEM are present in explanted, human invasive breast tumors, the density of TMEM correlates with the histologic grade of the tumors, and TMEM density is positively associated with the risk of developing distant organ metastases.

Materials and Methods

Preliminary to assessing TMEM density in cases with known outcome, macrophage and blood vessel density were evaluated in examples of benign and malignant breast tissue, and perivascular macrophage density and TMEM density were evaluated in a series of invasive ductal carcinomas without known outcome. These initial measurements were made to determine if any of the three markers used individually correlated with tumor grade, which may be used as a surrogate for clinical outcome. Thus, this study had three distinct components. Patient samples for each component were unique, and the case composition of each part is described below along with the associated methodology. All immunohistochemical (IHC) staining was performed on archival, paraffin-embedded tissue obtained from the archives of the Department of Pathology and Laboratory Medicine at New York-Presbyterian Hospital—Weill Cornell Medical College and used a Bond Max Autostainer and reagents (Vision Biosystems, Norwell, Mass.), unless otherwise specified. The modified Bloom-Richardson grading scheme was used to determine tumor grade/differentiation in all cases. Institutional Review Board approval was obtained for all parts of this study.

Evaluation of Macrophage and Blood Vessel Density in Benign and Malignant Breast Tissue.

Ten cases each of well, moderate, and poorly differentiated ductal carcinomas of the breast were evaluated for this part of the study. An additional ten cases each of ductal carcinoma in situ (DCIS) and benign macromastic breast tissue (obtained from reduction mammoplasties) were also included for comparison. Representative sections from each case were stained using double immunohistochemistry for CD68 (macrophage-specific) (Falini et al., 1993) and CD31 (endothelial cell-specific) (Parums et al., 1990). Five-micron-thick sections were deparaffinized and endogenous peroxidase was inactivated followed by antigen retrieval with Bond Epitope Retrieval Solution 1 according to the manufacturer's instructions. CD68 was detected by incubating slides with anti-CD68 monoclonal antibody (clone PG-M1, 1:300 dilution, Dako, Carpinteria, Calif.), followed by a polymer-based diaminobenzidine (DAB) colorimetric detection system according to manufacturer's instructions (Bond Polymer Detection Systems, Vision Biosystems). Antigen retrieval was performed a second time, and slides were incubated with anti-CD31 monoclonal antibody (Clone JC70A, 1:300 dilution, Dako) and detected using an alkaline phosphatase-based streptavidin/biotinylated link system and Permanent Red chromogen (all from Dako). Hematoxylin was used as counterstain.

Ten separate digital photographs were taken of each double IHC stained section at 200× magnification. For each picture, ten boxes were created, each box being approximately three cell diameters across and corresponding to the hypothesized area of a TMEM. Square boxes of 60 μm on a side were chosen and centered on epithelium, as epithelial cells are necessary for the definition of TMEM. For the invasive carcinomas, an additional ten boxes were centered on non-neoplastic epithelium adjacent to the tumor for comparison. Two pathologists randomly divided all cases and independently counted and recorded the number of macrophages and blood vessels in each box. The average of the ten boxes for each case was calculated. Differences in blood vessel density and macrophage density among the various tissue types were tested for statistical significance using the Wilcoxon Rank-Sum Test. Given that fifteen comparisons were performed, the p-value for determining statistical significance was set at 0.003 by applying the Bonferroni correction to the standard assumption that $p<0.05$ is statistically significant.

Evaluation of Perivascular Macrophage and TMEM Densities in Invasive Ductal Carcinomas.

Twenty cases each of well, moderate, and poorly differentiated ductal carcinomas of the breast were retrieved for inclusion in this portion of the study. Representative sections of each case were stained using triple immunohistochemistry. First, five-micron-thick sections were deparaffinized, endogenous peroxidase was inactivated, and antigen retrieval performed as described above. Next, CD68 was detected as described above. Slides were then subsequently incubated with anti-CD31 monoclonal antibody as above except that colorimetric detection was with Vector Blue (Vector Laboratories, Burlingame, Calif.). Finally, slides were subjected to antigen retrieval and incubated with anti-mena monoclonal antibody (Lebrand et al., 2004). Detection of mena used the Permanent Red chromogen as described above. Methylene green was used as a counterstain.

Five digital photographs of each triple IHC stained section were taken at 200× magnification. Two pathologists randomly divided the cases and tabulated for all images 1) the number of perivascular macrophages along a cumulative length of 200 μm of blood vessels and 2) the number of TMEM. The average values of these measures were then calculated for each case. TMEM was defined as the direct apposition of an invasive tumor cell (here expressing Mena), a macrophage, and an endothelial cell. The two pathologists achieved concordance on TMEM scoring using over 200 images from a series of ten test cases (random archival breast cancer specimens). Differences in perivascular macrophage density and TMEM density among the various tissue types were tested for statistical significance using the Wilcoxon Rank-Sum Test. Given that three comparisons were performed, the p-value for determining statistical significance was set at 0.017 by applying the Bonferroni correction to the standard assumption that $p<0.05$ is statistically significant.

Evaluation of TMEM in Patients with Known Clinical Outcome.

Utilizing the Cancer Registry at New York-Presbyterian Hospital/Weill Cornell Medical College, thirty patients with invasive ductal carcinoma of the breast who developed systemic, distant organ metastases were identified and one control was matched individually to each case. The controls had only localized disease (i.e., invasive ductal carcinoma limited to the breast or with regional lymph node metastasis only). All patients were female and underwent primary resection of their breast cancer at New York-Presbyterian Hospital between 1992 and 2003. A minimum clinical follow-up time of five years was required for inclusion, and the follow-up time for all non-metastatic patients was at least as long as that of their matched metastatic case. Due to the limited number of patients with metastatic, well differentiated carcinomas, only patients with moderately or poorly differentiated carcinomas were included. Matching of metastatic and non-metastatic patients was based upon well established prognostic factors including tumor grade (matched exactly), tumor size (categorized as <2 cm, 2-4 cm, and >4 cm), presence or absence of lymph node metastasis, and hormone receptor status.

For each patient, representative sections of tumor were subjected to triple IHC staining for CD68, CD31, and Mena, as described above. In each case, twenty high-power fields (400× total magnification) were evaluated for the total number of TMEM. Two pathologists each evaluated half of the cases (30 patient samples each). The cases were randomly distributed between the two pathologists, and both pathologists were blinded to the clinical outcome. After tabulation of TMEM for all samples, the cases were categorized according to whether they were metastatic and non-metastatic, and the difference in TMEM density between metastatic and non-metastatic patients was tested for statistical significance using the Wilcoxon Signed-Rank (Matched Pairs) Test. Differences in TMEM density among other variable groups (e.g., lymph node status) were tested for statistical significance using the Wilcoxon Rank Sum Test. Odds ratios and 95% confidence intervals for the association between TMEM count and risk of metastasis were estimated using conditional logistic regression.

Results

Macrophage Density, Blood Vessel Density and Mena Staining are not Individually Correlated with Tumor Grade.

Figure 2A:
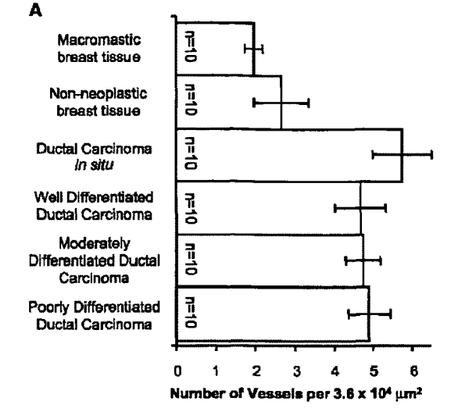
FIG. 2A-2D. Microvessel and macrophage density, perivascular macrophage density, and TMEM density in invasive ductal carcinomas. A. Microvessel density. The density of blood vessels is higher in DCIS and invasive carcinomas than in benign breast tissue, but there is little difference in the blood vessel density among the three grades of invasive tumor. B. Macrophage density. The density of macrophages increases from DCIS through the grades of invasive tumor, but the differences are not statistically significant and do not exceed the macrophage density of adjacent non-neoplastic breast tissue. C. Perivascular macrophage density. Evaluating the density of macrophages along blood vessels revealed no correlation between perivascular macrophage density and tumor grade. D. TMEM density. TMEM counts, however, clearly separate well differentiated from moderately ($p<0.008$) and poorly ($p<0.001$) differentiated carcinomas. TMEM is defined as the direct apposition of an endothelial cell, a macrophage, and an invasive tumor cell. Bars indicate standard error of the mean.
Figure 2B:
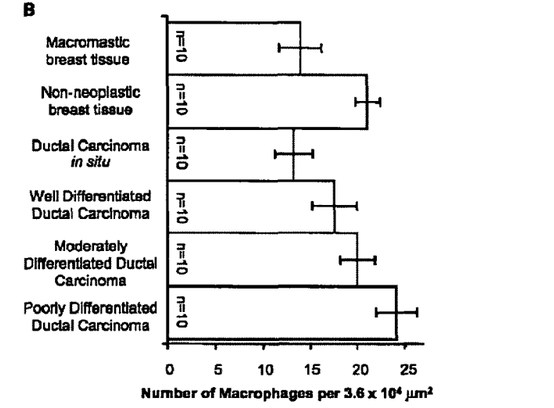

When quantified in the four types of breast tissue examined in this study—benign macromastic breast tissue, non-neoplastic breast tissue adjacent to carcinoma, in situ carcinoma, and invasive carcinomas—neither blood vessel nor macrophage density alone were good discriminators of benign from malignant breast tissue and did not vary substantially by tumor grade. Vessel counts overall were higher in the in situ and invasive tumors, but vessel density was similar in all three tumor grades (FIG. 2A). Regarding vessel density, the only statistically significant differences were between macromastic breast tissue and DCIS (p<0.001), macromastic breast tissue and moderately differentiated carcinoma (p<0.001), and macromastic breast tissue and poorly differentiated carcinoma (p<0.001). Macrophage density appeared to increase from in situ to invasive tumor and with increased histologic grade, but did not exceed the macrophage density of non-neoplastic breast tissue adjacent to tumor (FIG. 2B). Regarding macrophage density, the only statistically significant difference was between DCIS and poorly differentiated carcinoma (p<0.003).

Figure 2C:
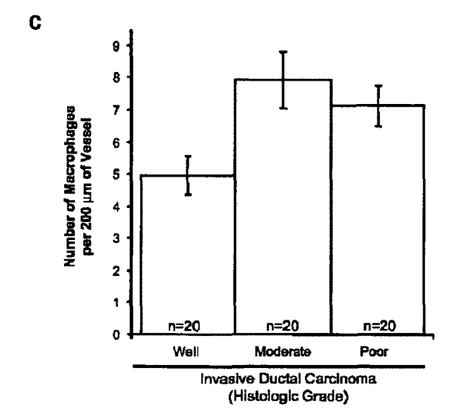

Additionally, perivascular macrophage density was also not associated with tumor grade. As evident in FIG. 2C, the number of macrophages along a blood vessel was not significantly different among the three grades of invasive tumor (p>0.02) for all comparisons).

Mena was generally expressed only at low levels, if at all, in non-neoplastic ducts and lobules. DCIS and invasive ductal carcinomas, however, contained substantially higher amounts of Mena protein. Mena expression was often heterogeneous within a given tumor, such that some carcinoma cells or regions of tumor were strongly positive while others showed a staining intensity similar to non-neoplastic epithelial cells. In all cases, the cellular distribution of Mena was diffusely cytoplasmic. Using standard IHC methods, patterns of subcellular localization of Mena could not be identified (e.g., lamellopodia).

Identification of TMEM in Histologic Sections.

Figure 3A:
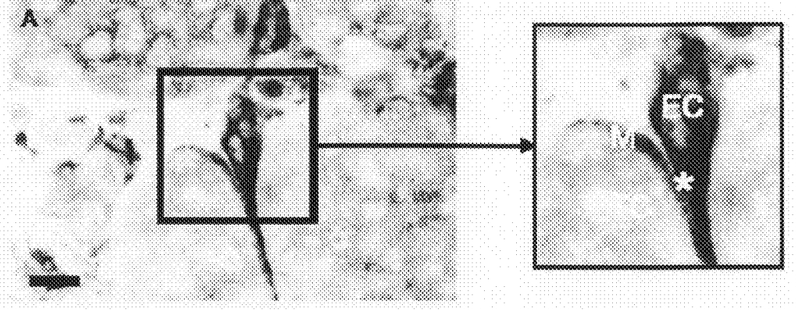
FIG. 3A-3C. Identification of TMEM in histologic sections. Different examples of TMEM as scored in histologic sections. The boxes depict the area of TMEM. In the enlarged images of the boxes, the asterisk (*) denotes the "epicenter" of the TMEM, where the three cell types are most intimately apposed. A. The blood vessel courses between nests of tumor cells. At the asterisk, the macrophage is interposed between the endothelial cell and tumor cell. B. The macrophage again is seen interposed between the tumor cell and endothelial cell at the site of the asterisk. In both panels A and B, the vessel is seen in longitudinal section. C. The same intimate relationship is seen between endothelial cell, macrophage, and tumor cell, but the vessel is seen in cross section. Note that in all the examples there is no collagen seen between the three cell types. In the triple immunostain in the present study, macrophages are brown, endothelial cells are blue, and tumor cells expressing Mena are red. EC—endothelial cell, M—macrophage, TC—tumor cell. Calibration bar is 20 µm.
Figure 3B:
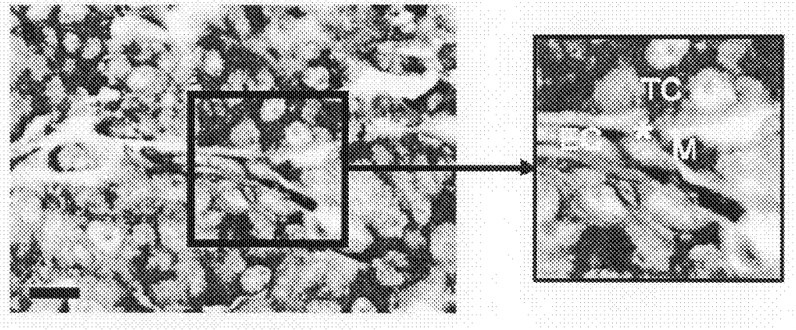
Figure 3C:
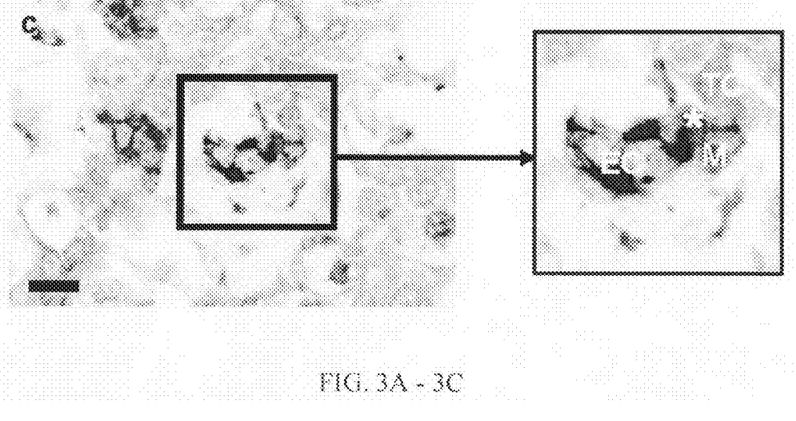

FIG. 3 provides illustrations of TMEM as seen in paraffin-embedded, immunohistochemically stained tissue sections. By definition, to qualify as a TMEM, an endothelial cell, a macrophage, and an invasive tumor cell must be in direct apposition. All of the stains are cytoplasmic. Endothelial cells often stain with a smooth linear quality, whereas the macrophages typically show a more granular staining pattern. At low power, if a tumor contains an abundance of collagen and is relatively avascular, the TMEM count is likely to be low. Alternatively, if one sees vessels coursing through nests of tumor cells, high power examination may reveal macrophages in apposition to these vessels and tumor cells, thus qualifying as TMEMs. As the various panels of FIG. 3 show, vessels may be cut longitudinally or in cross section. If collagen fibers were present between a perivascular macrophage and the tumor cells, TMEM was not scored. Additionally, if the endothelial cells and macrophages were not apposed, the definition of TMEM was also not met. Another observation was that TMEM were not localized preferentially to the central or peripheral aspects of the tumor. Rather they were distributed uniformly across an entire tumor. Typically they were found as single structures scattered throughout the carcinoma. In tumors that contained "hot spots," or clusters of TMEM along a single vessel, the overall TMEM counts were high.

TMEM Counts are Associated with Tumor Grade.

Figure 2D:
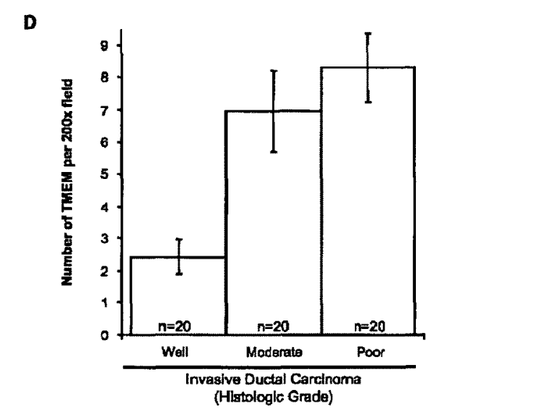

The number of TMEMs in the well-differentiated tumors was significantly lower than those in moderately and poorly differentiated tumors (p<0.008 and p<0.001, respectively) (FIG. 2D). What was frequently observed in well-differentiated tumors was a total lack of endothelial cells in any proximity to either tumor cells or macrophages. In these fields, the TMEM score was zero. Within the moderately and poorly differentiated groups, however, there was a range in the numbers of TMEMs identified, but the differences in TMEM counts between these two groups was not significant (p>0.02).

TMEM Density in Patients with Known Clinical Outcome.

The clinicopathologic characteristics for the metastatic and non-metastatic patients in the case-control study are presented in Table 1. Each paired metastatic and non-metastatic patient was matched as closely as possible for the parameters listed, and, as such, differences between the two groups with respect to these characteristics are not statistically significant.

Figure 4A:
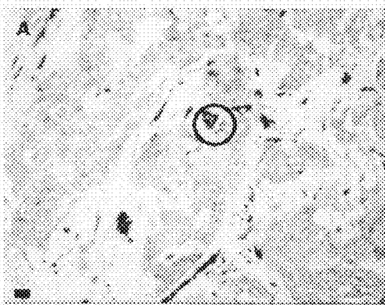
FIG. 4A-4D. TMEM density in metastatic and non-metastatic patients. A-B. Both tumors depicted in A and B are of similar grade and are shown using the triple immunostain described herein. A is an example of a non-metastatic case, where TMEM counts (depicted by circles), tend to be low. B, on the other hand, is from a patient who developed distant organ metastases, and the TMEM density is high. While the cases in panels A and B are at the extreme of low and high TMEM density, they are included for comparison given their strikingly similar histology yet disparate TMEM counts, which reinforces the novelty and utility of the triple immunostain in identifying TMEM in the present study. C. Scatter plot depicting the results for all sixty patients included in the case control study. D. Difference between metastic and non-metastic TMEM values for each of 30 individually matched pairs of subject. Original magnification=400×; bars in A and B=20 microns.
Figure 4B:
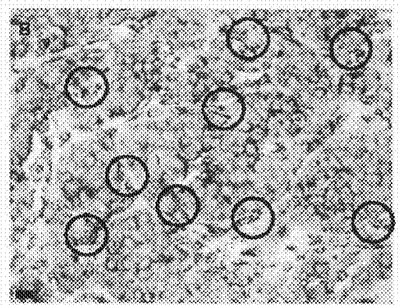
Figure 4C:
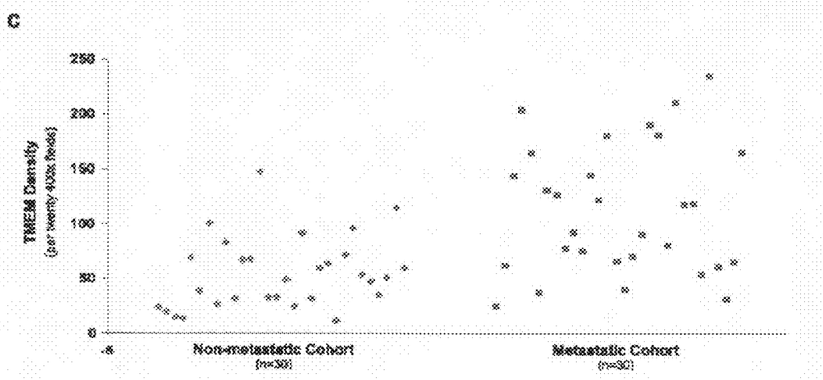
Figure 4D:
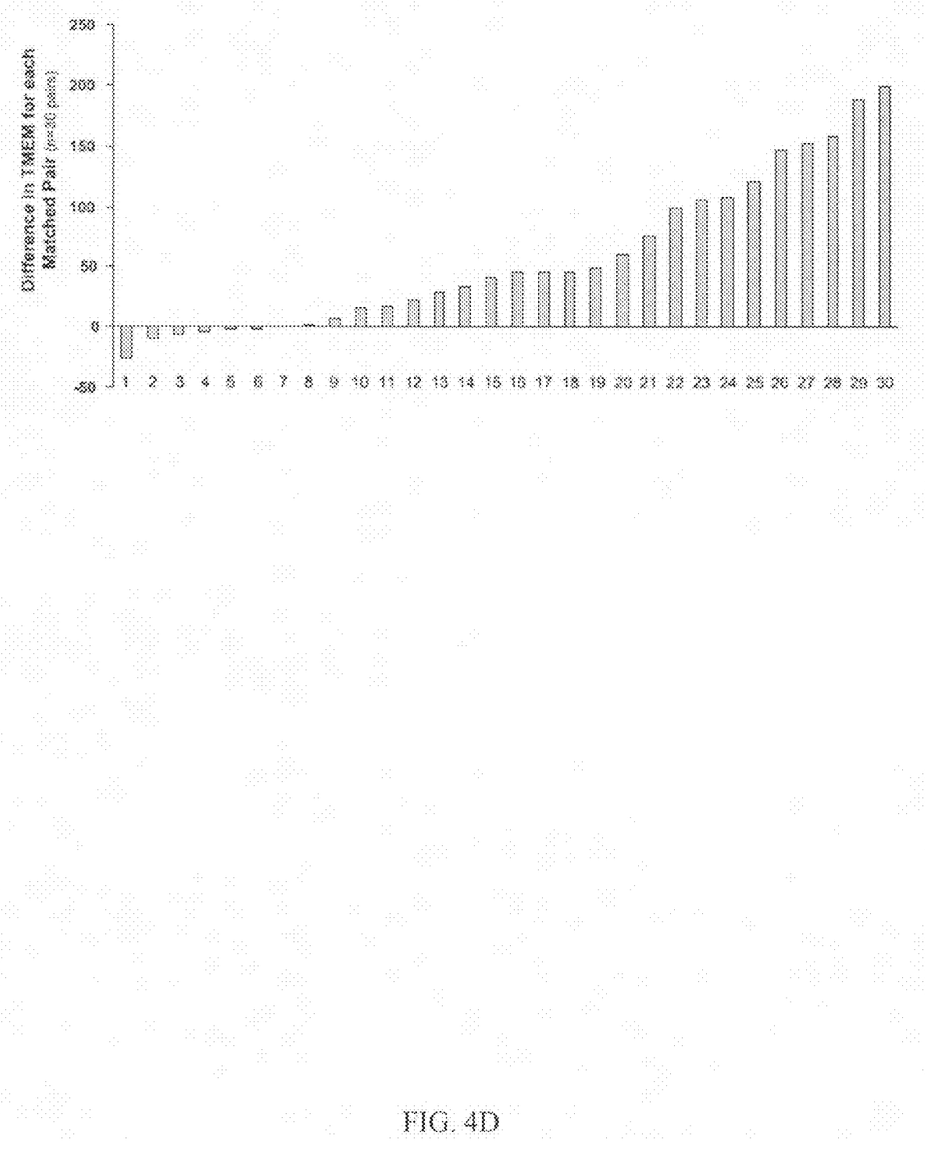

FIG. 4A is a representative image from a non-metastatic patient, while FIG. 4B depicts a representative image from a patient who developed systemic metastasis. In both images, TMEMs are denoted by circles. The individual TMEM densities for all 60 patients are depicted in FIG. 4C as a scatter plot. In FIG. 4D, each of the 30 matched pairs is considered separately, and the difference between individual metastatic and non metastatic pairing is shown. The median ($5^{th}$ percentile, $95^{th}$ percentile) between the metastatic cases and their matched non metastatic controls with respect to TMEM score was 43.5 (−17.1, 192) indicating that in general the metastatic cases have substantially higher TMEM scores than their matched controls.

TMEM density was significantly greater in the group of breast cancer patients who developed distant organ metastases as compared to those with only localized disease (mean=105 vs. 50, respectively, p=0.00006) (Table 2A). For every 10-unit increase in the TMEM count, the risk of systemic metastasis increased by 90% [Odds ratio (OR) 1.9; 95% confidence interval (CI) 1.1-3.4]. This estimate was robust to adjustment (separately) for age at diagnosis, tumor grade, tumor size, lymphovascular invasion, number of lymph nodes containing metastatic carcinoma, estrogen receptor (ER) status, progesterone receptor status, and Her2/neu status (Table 2B). TMEM densities for each prognostic subgroup (e.g., ER-positive versus ER-negative patients) did not differ significantly and are provided in Table 3.

TABLE 1

Clinicopathologic characteristics for the metastatic and non-metastatic patients.

| | Metastatic (n = 30) | Non-metastatic (n = 30) | P |
|---|---|---|---|
| Age at diagnosis (yrs), mean (range) | 53.1 (29-88) | 52.6 (30-81) | NS |
| Tumor grade, no. (%) | | | |
| Moderate | 12 (40) | 12 (40) | NS |
| Poor | 18 (60) | 18 (60) | NS |
| Tumor Size (cm), mean (range) | 3.5 (1-11) | 3.7 (1-10) | NS |
| Lymph node metastasis, present, no. (%) | 20 (67) | 19 (63) | NS |
| No. lymph nodes positive, mean (range) | 4.7 (0-17) | 4.3 (0-14) | NS |
| Lymphovascular invasion, present, no. (%) | 18 (60) | 11 (37) | NS |
| Hormone Status, no. (%) | | | |
| Estrogen receptor-positive | 19 (63) | 18 (60) | NS |
| Progesterone receptor-positive | 11 (37) | 15 (50) | NS |
| Her2/neu overexpression, present, no. (%) | 9 (30) | 7 (23) | NS |

A search of the Cancer Registry data base of the New York-Presbyterian Hospital/Weill Cornell Medical Center from 1992-2003 yielded thirty patients with known metastatic disease who had undergone primary resection of their breast cancer at New York-Presbyterian Hospital. The same data base was then searched to identify a matched non-metastatic control. The controls were matched for each of the parameters listed above. There was a minimum follow up time of five years for all cases, and the follow up time for each control was at least as long as the follow up time for its metastatic pair. NS, not significant; P > 0.05.

TABLE 2

Case-control study results.

(A) TMEM Density

| | Metastatic Patients (n = 30) | Non-metastatic Patients (n = 30) | P |
|---|---|---|---|
| Median ($5^{th}$, $95^{th}$ percentile) | 105 (28.3, 221) | 50 (13.1, 130) | 0.00006 |

(B) Increase in risk of metastasis per 10 unit increase in TMEM

| Adjusted for | Odds Ratio | 95% CI |
|---|---|---|
| (Unadjusted) | 1.9 | 1.1-3.4 |
| Age at diagnosis | 1.9 | 1.1-3.4 |

TABLE 2-continued

Case-control study results.

| | | |
|---|---|---|
| Tumor grade | 1.9 | 1.1-3.4 |
| Tumor size | 1.9 | 1.1-3.3 |
| Lymphovascular invasion | 1.5 | 0.95-2.3 |
| Lymph node metastasis | 1.9 | 1.0-3.6 |
| Estrogen receptor status | 2.0 | 1.1-3.7 |
| Progesterone receptor status | 1.9 | 1.0-3.6 |
| HER-2/neu status | 2.2 | 1.1-4.7 |

TMEM density was significantly higher in the group of patients who developed distant metastasis compared to those with only localized breast cancer (A). Additionally, for every ten unit increase in TMEM, the risk of metastasis increased 90% (B). This estimate was robust to adjustment (separately) for the commonly used prognostic criteria listed in the table, including tumor grade, emphasizing that TMEM is not a surrogate for grade and may be used as an independent prognostic factor. CI = confidence interval.

TABLE 3

TMEM densities for each prognostic subgroup.

| | Metastastic patients | | Non-metastatic patients | |
|---|---|---|---|---|
| | TMEM Density Mean (SEM) | P | TMEM Density Mean (SEM) | P |
| Tumor differentiation | | NS | | NS |
| Moderate | 100 (19) | | 44 (8.3) | |
| Poor | 120 (13) | | 61.7 (8) | |
| Tumor size | | NS | | NS |
| <2 cm | 112 (19) | | 66 (14) | |
| 2-4 cm | 98.4 (15) | | 54.5 (9.4) | |
| >4 cm | 129 (24) | | 51.3 (8.8) | |
| Lymph node metastasis | | NS | | NS |
| Present | 98.9 (14) | | 57.4 (8.1) | |
| Absent | 137 (15) | | 49.8 (9.9) | |
| No. lymph nodes positive | | NS | | NS |
| <5 nodes | 105 (21) | | 62.4 (17) | |
| ≥5 nodes | 91 (18) | | 54.5 (7.2) | |
| Lymphovascular invasion | | NS | | NS |
| Present | 91.5 (12) | | 55.1 (11) | |
| Absent | 141 (19) | | 54.2 (10) | |
| Estrogen receptor status | | NS | | NS |
| Positive | 123 (15) | | 52.9 (7) | |
| Negative | 91.5 (13) | | 57.2 (11) | |
| Progesterone receptor status | | NS | | NS |
| Positive | 118 (20) | | 48 (7.6) | |
| Negative | 108 (13) | | 61 (9.1) | |
| HER-2/neu overexpression | | NS | | NS |
| Present | 118 (20) | | 37.1 (8) | |
| Absent | 109 (13) | | 59.9 (7.1) | |

TMEM density was not associated with any of the prognostic criteria examined in this study, indicating TMEM is an independent predictor of metastatic potential. SEM = standard error of the mean; NS = not significant; p ≥ 0.05.

Discussion

Although the major cause of mortality in breast cancer is hematogenous metastasis, there have been no reliable methodologies to predict the risk for metastatic disease. Intravital imaging of invasive tumor cell behavior in mammary tumors in rats and mice has revealed a direct role for macrophages in tumor cell invasion and intravasation (Wyckoff et al. 2004, 2007). High resolution two-photon imaging of the interactions between perivascular macrophages and tumor cells during intravasation in mouse models of metastatic mammary carcinoma has revealed the presence of a microanatomic compartment that defines the site where intravasation by motile carcinoma cells occurs. This compartment is referred to in the present study as TMEM. The constituent cells of TMEM are an endothelial cell, a perivascular macrophage, and an invasive Mena-expressing tumor cell. Mena, a member of the Ena/VASP protein family, has been identified as an upregulated gene in the invasive migratory subpopulation of tumor cells in animal models of breast cancer (Wang et al. 2004, 2007). Mena has been shown to regulate actin-driven cellular protrusions and cell motility in a variety of cell types (Barzik et al., 2005, Gertler et al. 1996, Goswami et al. 2009, Krause et al. 2003, Philippar et al. 2008, Wyckoff et al. 2004), to be up-regulated in circulating tumor cells (Goswami et al. 2009) and in primary human breast cancers (Di Modugno et al. 2004, 2006) and to sensitize tumor cells to epidermal growth factor (EGF) signals and increase metastasis (Philippar et al. 2008). Hence, Mena has been postulated to be a marker for invasive, migratory tumor cells and metastatic potential (Goswami et al. 2009, Philippar et al. 2008).

In initial studies, tumor grade was used as a surrogate for prognosis (including metastasis) and individual components of TMEM alone were investigated as predictive of poor outcome. To evaluate these components, invasive tumor cells expressing Mena, blood vessel density, and macrophage density were examined. Mena expression was higher in tumors as compared to benign epithelial cells, but did not differ among the three grades of invasive carcinoma. Furthermore, the staining intensity was heterogeneous within any given tumor. With regard to macrophage and blood vessel density, while there are studies on human breast cancer suggesting an association between increased densities and poor outcome (Condeelis et al. 2006, Wyckoff et al. 2007), the significance of these counts as independent predictors has not been clearly demonstrated. A link between macrophage density and poor prognosis, for example, may be evident only in the context of other currently accepted and more frequently used prognostic markers, such as lymph node metastasis, tumor grade, and hormone receptor status (Tsutsui et al. 2005). Similarly, when microvessel density is associated with prognosis, it is also in the context of tumor grade and lymphovascular invasion (Dhakai et al., 2008, Hansen et al. 2004). Microvessel density was generally elevated in the carcinomas compared to benign breast tissue, but this observation was not statistically significant, perhaps reflecting the relatively small sample size. Additionally, increasing blood vessel density was not significantly associated with increasing tumor grade. Macrophage density also tended to increase with tumor grade, but this trend again was not statistically significant.

Because tumor cells in in vivo animal models show greatest motility and intravasation in association with perivascular macrophages (Wang et al. 2004, Wyckoff et al. 2004, 2007), it was next assessed whether perivascular macrophage density might correlate better with tumor grade. What was found, however, was that the number of macrophages along a blood vessel, at least in invasive carcinomas, appears to be relatively constant, regardless of grade.

Given the above results, then, it was concluded that the individual components of the proposed microenvironment (microvessel density, macrophage density, and Mena expression) and one relational component (perivascular macrophage density) were not associated with tumor grade, and, therefore, not likely to be of prognostic benefit.

When all the components were looked at together, however, the results were indicative of an association with risk of tumor progression. Defining TMEM as a perivascular macrophage in direct apposition to a Mena-expressing tumor cell, TMEM counts differed significantly between well vs. moderately and poorly differentiated tumors. In well differentiated tumors, where the outcome is generally good, the TMEM count was low. In moderately and poorly differentiated tumors, there was a wide range in TMEM counts, but overall the TMEM counts were much higher than in the well differentiated tumors. Since grade is only a surrogate for metastatic risk, finding a range is not surprising. Some moderately and poorly differentiated tumors metastasize, while others do not. However, very few well differentiated tumors metastasize, and the overall TMEM counts were low in this group with a relatively small range.

For completeness, the staining patterns for Mena, macrophages, and endothelial cells in DCIS and non-neoplastic breast tissue were also examined. Not surprisingly, TMEM was not found in either tissue type. In benign breast tissue, there are no cancer cells, and in DCIS, the cells are noninvasive. The epithelial cells of DCIS and benign breast tissue are physically unable to appose perivascular macrophages due to an intact basement membrane as well as a layer of myoepithelial cells.

In the animal models, intravasation of tumor cells observed by direct imaging requires the direct interaction between invasive tumor cells and perivascular macrophages through a paracrine signaling loop (Wyckoff et al. 2004, 2007) and the presence of this microanatomic compartment is associated with the presence of intravascular tumor cell burden and metastasis (Wyckoff et al. 2007). In the present study of human breast cancer samples, then, the next step was to evaluate TMEM in a case-control study of metastatic and non-metastatic breast cancers. Thirty breast cancer patients were identified with known distant metastases and matched with thirty patients with breast cancer who had not developed metastasis from hematogenous spread. Using the same immunohistochemical triple stain, TMEMs were quantified in the same fashion as for the case series of well, moderate, and poorly differentiated tumors. Well differentiated tumors were not included due to lack of availability of metastatic samples (only two cases identified). For the series of matched pairs of moderately and poorly differentiated tumors, the difference in TMEM counts between metastatic and non-metastatic tumors was substantial (median=105 vs. 50, respectively; p=0.00006). The results indicate that TMEM density at initial cancer resection was associated with risk of metastasis. Specifically, for an increase in the TMEM count of 10, the risk of metastasis nearly doubled. The ability of TMEM density to predict systemic spread of carcinoma cells was independent of other currently used prognosticators, including lymph node metastasis, tumor size, the presence of lymphovascular invasion, and tumor grade, although the sample size for this study precluded simultaneous adjustment for all of these factors.

To date, no method for predicting metastatic risk exists that draws upon the in vivo observation of hematogenous metastasis in animal models. These results suggest that the mechanism of hematogenous dissemination in humans is likely similar to that seen in rodent models, where tumor cells intravasate in association with perivascular macrophages. TMEM is expected to be a powerful addition to the current approach for assessing metastatic risk and the need for systemic chemotherapy. If patients can be better classified as either low-risk or high-risk for metastasis, customized (patient-tailored) therapies can be designed to prevent over-treatment and under-treatment of patients, respectively.

REFERENCES

Barzik M, Kotova T I, Higgs H N et al. Ena/VASP proteins enhance actin polymerization in the presence of barbed end capping proteins. J Biol Chem 2005; 280:28653-62.

Bingle L, Brown N J, Lewis C E. The role of tumour-associated macrophages in tumour progression: implications for new anticancer therapies. J Pathol 2002; 196:254-65.

Condeelis J, Pollard J W. Macrophages: obligate partners for tumor cell migration, invasion, and metastasis. Cell 2006; 124:263-6.

Condeelis J, Singer R H, Segall J E. The great escape: when cancer cells hijack the genes for chemotaxis and motility. Annu Rev Cell Dev Biol. 2005; 21: 695-718.

Dhakal H P, Naume B, Synnestvedt M et al. Vascularization in Primary Breast Carcinomas: Its Prognostic Significance and Relationship with Tumor Cell Dissemination. Clin Cancer Res 2008; 14:2341-50.

Di Modugno F, Bronzi G, Scanlan M J et al. Human Mena protein, a serex-defined antigen overexpressed in breast cancer eliciting both humoral and CD8+ T-cell immune response. Int J Cancer 2004; 109:909-18.

Di Modugno F, Mottolese M, Di Benedetto A et al. The cytoskeleton regulatory protein hMena (ENAH) is overexpressed in human benign breast lesions with high risk of transformation and human epidermal growth factor receptor-2-positive/hormonal receptor-negative tumors. Clin Cancer Res 2006; 12:1470-8.

Di Modugno F, DeMonte L, Balsamo M et al. Molecular cloning of hMena (ENAH) and its splice variant hMena+11a: epidermal growth factor increases their expression and stimulates hMena+11a phosphorylation in breast cancer cell lines. Cancer Res 2007; 67:2657-65.

Falini B, Flenghi L, Pileri S et al. PG-M1: a new monoclonal antibody directed against a fixative-resistant epitope on the macrophage-restricted form of the CD68 molecule. Am J Pathol 1993; 142:1359-72.

Gertler F B, Niebuhr K, Reinhard M, Wehland J, Soriano P. Mena, a relative of VASP and Drosophila Enabled, is implicated in the control of microfilament dynamics. Cell 1996; 87:227-39.

Gotswami S, Ulrike P, Sun D, Patsialou A, Avraham J, Wang W, Di Modugno F, Nistico P, Gertler F, Condeelis J. Identification of invasion specific splice variants of the cytoskeletal protein Mena present in mammary tumor cells during invasion in vivo. Clin Exp Metastasis 2009; 26: 153-59.

Hansen S, Sorensen F B, Vach W, Grabau D A, Bak M, Rose C. Microvessel density compared with the Chalkley count in a prognostic study of angiogenesis in breast cancer patients. Histopathology 2004; 44:428-36.

Krause M, Dent E W, Bear J E, Loureiro J J, Gertler F B. Ena/VASP proteins: regulators of the actin cytoskeleton and cell migration. Annu Rev Cell Dev Biol 2003; 19:541-64.

Lebrand C, Dent E W, Strasser G A et al. Critical role of Ena/VASP proteins for filopodia formation in neurons and in function downstream of netrin-1. Neuron 2004; 42:37-49.

Lin E Y, Nguyen A V, Russell R G, Pollard J W. Colony-stimulating factor 1 promotes progression of mammary tumors to malignancy. J Exp Med 2001; 193:727-40.

Parums D V, Cordell J L, Micklem K, Heryet A R, Gatter K C, Mason D Y. JC70A: a new monoclonal antibody that detects vascular endothelium associated antigen on routinely processed tissue sections. J Clin Pathol 1990; 43:752-7.

Philippar U, Evanthia T. Roussos, Matthew Oser, Hideki Yamaguchi, Hyung-Do Kim, Silvia Giampieri, Yarong Wang, Sumanta Goswami, Jeffrey B. Wyckoff, Douglas A. Lauffenburger, Erik Sahai, John S. Condeelis and Frank B.

Gertler. A Mena invasion isoform potentiates EGF-induced carcinoma cell invasion and metastasis. Dev. Cell 2008; 15: 813-28.

Ries LAG, Melbert D, Krapcho M et al (Eds.). SEER Cancer Statistics Review, 1975-2004, National Cancer Institute. Bethesda, Md., http://seer.cancer.gov/csr/1975_2004/, based on November 2006 SEER data submission, posted to the SEER web site, 2007.

Tsutsui S, Yasuda K, Suzuki K, Tahara K, Higashi H, Era S. Macrophage infiltration and its prognostic implications in breast cancer: the relationship with VEGF expression and microvessel density. Oncol Rep 2005; 14:425-31.

Wang W, Goswami S, Lapidus K et al. Identification and testing of a gene expression signature of invasive carcinoma cells within primary mammary tumors. Cancer Res 2004; 64(23):8585-94.

Wang W, Wyckoff J B, Goswami S et al. Coordinated regulation of pathways for enhanced cell motility and chemotaxis is conserved in rat and mouse mammary tumors. Cancer Res 2007; 67:3505-11.

Weigelt B, Peterse J L, van't Veer L J. Breast cancer metastasis: markers and models. Nat Rev Cancer 2005; 5:591-602.

Wyckoff J, Wang W, Lin E Y, et al. A paracrine loop between tumor cells and macrophages is required for tumor cell migration in mammary tumors. Cancer Res 2004; 64:7022-9.

Wyckoff J B, Wang Y, Lin E Y et al. Direct visualization of macrophage-assisted tumor cell motility and intravasation in mammary tumors. Cancer Res 2007; 67:2649-56.

PCT International Publication No. WO 2008/097466, published Aug. 14, 2008, Metastasis Specific Splice Variants of Mena and Uses Thereof in Diagnosis, Prognosis and Treatment of Tumors.

What is claimed is:

1. A method for determining the risk of tumor cells from a subject undergoing hematogenous metastasis comprising:
   treating a tumor sample from the subject to detect endothelial cells, macrophages, and invasive tumor cells in the tumor sample,
   determining whether or not an endothelial cell, a macrophage, and an invasive tumor cell are in direct contact in the tumor sample, and
   counting the number of occurrences that an endothelial cell, a macrophage, and an invasive tumor cell are in direct contact in the tumor sample,
   wherein the risk of tumor cells undergoing hematogenous metastasis increases with an increase in density of occurrences of an endothelial cell, a macrophage, and an invasive tumor cell in direct contact in the tumor sample.

2. The method of claim 1, wherein the endothelial cell is detected by detecting CD31.

3. The method of claim 1, wherein the macrophage is detected by detecting CD68.

4. The method of claim 1, wherein the invasive tumor cell is detected by detecting expression of Mena.

5. The method of claim 4, wherein the +++ variant and/or ++ variant of Mena is detected.

6. The method of claim 4, wherein expression of Mena, Mena+++ and/or Mena++ is compared to expression of Mena 11a.

7. The method of claim 1, wherein the presence of the endothelial cell, the macrophage, and the invasive tumor cell is detected using triple immunohistochemistry.

8. The method of claim 1, wherein the risk of a tumor undergoing hematogenous metastasis in a subject approximately doubles for each additional ten times an endothelial cell, a macrophage, and an invasive tumor cell are found in direct contact in the tumor.

9. The method of claim 1, wherein the tumor is a breast, pancreas, prostate, colon, brain, liver, lung, head or neck tumor.

10. The method of claim 1, wherein the tumor is a breast tumor.

11. The method of claim 1, wherein endothelial cells, macrophages, and/or invasive tumor cells are detected using antibodies, monoclonal antibodies, antibody fragments, peptides and/or aptamers.

12. The method of claim 1, wherein multiple images of the tumor sample are analyzed for an occurrence of an endothelial cell, a macrophage, and an invasive tumor cell in direct contact in the tumor sample.

13. A method for determining a course of treatment for a tumor for a subject, the method comprising:
   treating a tumor sample from the subject to detect endothelial cells, macrophages, and invasive tumor cells in the tumor sample,
   determining whether or not an endothelial cell, a macrophage, and an invasive tumor cell are in direct contact in the tumor sample, and
   counting the number of occurrences that an endothelial cell, a macrophage, and an invasive tumor cell are in direct contact in the tumor sample,
   wherein an occurrence of an endothelial cell, a macrophage, and an invasive tumor cell in direct contact in the tumor sample indicates that the subject is at increased risk of hematogenous metastasis and should be treated for a metastatic tumor or wherein a lack of occurrence of an endothelial cell, a macrophage, and an invasive tumor cell in direct contact in the tumor sample indicates that the subject is at little risk of hematogenous metastasis and may not need to be treated for a metastatic tumor.

14. The method of claim 13, wherein the endothelial cell is detected by detecting CD31.

15. The method of claim 13, wherein the macrophage is detected by detecting CD68.

16. The method of claim 13, wherein the invasive tumor cell is detected by detecting expression of Mena.

17. The method of claim 16, wherein the +++ variant and/or ++ variant of Mena is detected.

18. The method of claim 16, wherein expression of Mena, Mena+++ and/or Mena++ is compared to expression of Mena 11a.

19. The method of claim 13, wherein the presence of the endothelial cell, the macrophage, and the invasive tumor cell is detected using triple immunohistochemistry.

20. The method of claim 13, wherein the risk of a tumor undergoing hematogenous metastasis in a subject approximately doubles for each additional ten times an endothelial cell, a macrophage, and an invasive tumor cell are found in direct contact in the tumor.

21. The method of claim 13, wherein the tumor is a breast, pancreas, prostate, colon, brain, liver, lung, head or neck tumor.

22. The method of claim 13, wherein the tumor is a breast tumor.

23. The method of claim 13, wherein endothelial cells, macrophages, and/or invasive tumor cells are detected using antibodies, monoclonal antibodies, antibody fragments, peptides and/or aptamers.

24. The method of claim 13, wherein multiple images of the tumor sample are analyzed for an occurrence of an endothelial cell, a macrophage, and an invasive tumor cell in direct contact in the tumor sample.

25. A kit for determining the risk of tumor cells undergoing hematogenous metastasis comprising an agent that specifically binds to CD31 for detecting endothelial cells, an agent that specifically binds to CD68 for detecting macrophages, and an agent that specifically binds to Mena for detecting an invasive tumor cell.

26. The kit of claim 25 comprising one or more agent that specifically binds to Mena+++, Mena++ or Mena 11a.

27. The kit of claim 25, wherein the agents are antibodies, monoclonal antibodies, antibody fragments, peptides and/or aptamers.

* * * * *